Feb. 5, 1974 G. C. KOHL Re. 27,915
CERVICAL BIOPSY-SAMPLING INSTRUMENT
Original Filed Feb. 29, 1968
Fig. 4.
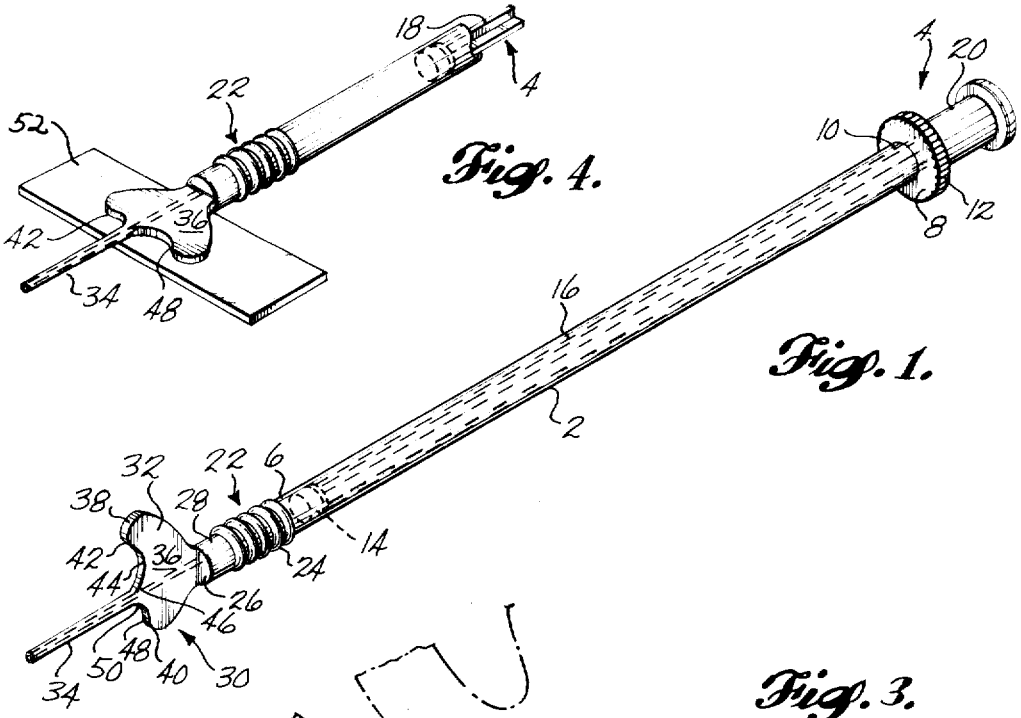
Fig. 1.
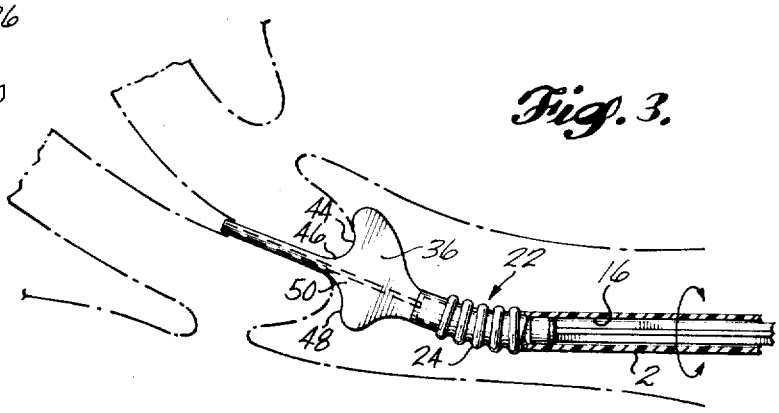
Fig. 3.
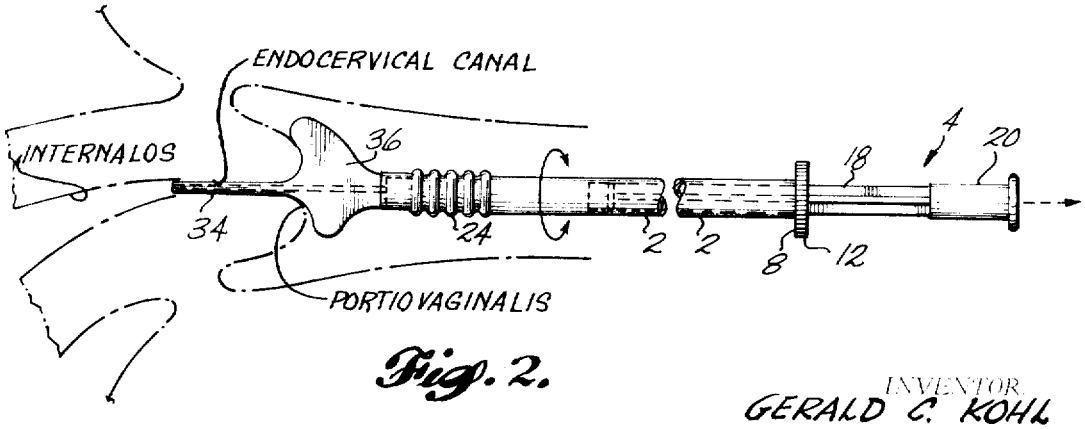
Fig. 2.
INVENTOR
GERALD C. KOHL
BY
Christensen, Sanborn & Matthews
ATTORNEYS United States Patent Office Re. 27,915
Reissued Feb. 5, 1974

27,915

CERVICAL BIOPSY-SAMPLING INSTRUMENT

Gerald C. Kohl, Tacoma, Wash., assignor to Medics Research and Development, Inc., Spokane, Wash.

No Drawing. Original No. 3,554,185, dated Jan. 12, 1974, Ser. No. 709,470, Feb. 29, 1968. Application for reissue Nov. 29, 1972, Ser. No. 310,387
Int. Cl. A61b *10/00*
US. Cl. 128—2 B 7 Claims

Matter enclosed in heavy brackets [ ] appears in the original patent but forms no part of this reissue specification; matter printed in italics indicates the additions made by reissue.

ABSTRACT OF THE DISCLOSURE

A cervical biopsy-sampling instrument is disclosed which comprises an aspirator having a spatulated sampling tip thereon by which a mucus aspirate and surface scrapings are collected from the cervix for cytological diagnosis. The tip is flexibly connected with the aspirator so that it can follow the relative deflection of the cervical canal when the canal is out of alignment with the vaginal canal. In addition, the scraping edge of the tip is defined on at least one side by a profile face of the tip which is substantially flat over the entire profile on that side, so that edge and face of the tip can be applied to a smear plate in the manner of a spatula for purposes of transferring the scrapings directly to the plate from the tip.

FIELD OF THE INVENTION

This invention relates to medical sampling instruments, and more particularly to medical sampling instruments for collecting tissue cell specimens from the female cervix for cytological diagnosis.

BACKGROUND OF THE INVENTION INCLUDING CERTAIN OBJECTS THEREOF

In collecting specimens of this nature in the past, scrapers have been used to collect cells from the surfaces of the endocervical canal and the portio vaginalis. In addition, aspirator pipettes have been used to collect a mucus specimen from the internal os of the cervix on the theory that the combined specimens allow for a more comprehensive diagnosis. In recent years, moreover, instruments have been proposed wherein a scraper edge is combined with an aspirator pipette to enable the two specimens to be taken simultaneously. Unfortunately, however, these dual-purpose instruments have not been commercially acceptable in that they require an additional instrument such as a spatula, with which to transfer the collected scrapings to a smear plate. They also lack the flexibility necessary to execute the sampling operation without discomfort to the patient and without abrading the surfaces of the cervix to the extent that the specimen is spoiled by an excessive blood accumulation. In fact, the task of executing the sampling operation with one of these dual-purpose instruments, and then transferring the specimen to the smear plate, has proven to be so delicate and time consuming a procedure that until the time of the present invention the art had continued to use the single purpose scraping and pipette devices known theretofor.

One object of the present invention, therefore, is to devise a dual-purpose instrument of this nature which is capable of collecting both mucus and scrapings in the manner of the earlier instruments, but which is free from the drawbacks which characterized these earlier instruments as mentioned above. Another object is to devise an instrument of this nature which is equipped with a sampling tip that operates not only as a means of gathering scrapings and mucus in the manner described, but also as a means of applying and spreading the collected material over the surface of a smear plate, so as to eliminate the necessity for an additional instrument and an intermediate transfer step. A third object is to provide an instrument of this nature which is equipped with a sampling tip that is capable of limited transverse flexure in relation to the aspirator so as to follow the relative deflection of the cervical canal when it is not aligned with the vaginal canal. A still further object is to provide an instrument of this nature in which the sampling tip is also capable of limited axial flexure in relation to the aspirator so as to cushion the initial impact of the tip on the cervix and the subsequent application of it to the cervix as a scraper. Other objects include the provision of an instrument of this nature which is inexpensive to manufacture and in fact so inexpensive as to be disposable after each operation; and which is capable of collecting the specimen without discomfort and trauma to the patient and without contaminating or otherwise spoiling the reliability of the specimen. Still further objects will appear from the description of the invention which follows hereafter.

SUMMARY OF THE INVENTION

These objects and advantages are realized by a cervical biopsy-sampling instrument of my invention which comprises an aspirator tube having a plunger therein, and a spatulated sampling tip formed on the distal end thereof to serve both as the means of collecting the specimen or specimens, and as the means of applying them to one or more smear plates. The tip is flexibly connected with the distal end of the tube, and has a relatively forward edge thereon which is relatively transversely disposed to the tube and operates as the scraping edge for the instrument. An elongated pipette extends through the scraping edge from a point of communication with the tube, and projects relatively forwardly from the edge for insertion in the cervical canal. When inserted, the pipette serves as a means of gathering a mucus specimen from the internal os of the cervix, and also as a pivot about which the scraping edge is applied to the portio vaginalis. Preferably, the tip is capable of both limited transverse and limited axial flexure with respect to the tube. I also prefer to form the tip so that the scraping edge is defined on at least one side by a profile face of the tip which is substantially parallel to the pipette and substantially flat over the entire profile of the tip on that side. In this way, the edge and face of the tip can be applied to the smear plate in the manner of a spatula for purposes of transferring the scrapings to the plate from the tip. The edge and face of the tip can also be employed to spread the scrapings over the surface of the plate. The muscus specimen collected through the pipette may be applied to the same plate with the scrapings or to a separate plate. In either case the aforesaid edge and face of the tip can also be employed to spread the mucus specimen over the surface of its plate in the same manner as with the scrapings.

The presently preferred embodiments of my invention employ a tip which has a smoothly curved indentation in the scraping edge thereof. The indentation is disposed adjacent to the pipette and conforms to the rounded contour of the portio vaginalis. The valley of the indentation is interconnected with the forwardly projecting portion of the pipette by means of a smoothly curved fillet which projects to a slight extent into the endocervical canal with the pipette.

These embodiments also employ a flexible sleeve as the means of interconnecting the tip with the distal end of the tube. The sleeve is corrugated so as to allow for both limited transverse and limited axial movement of the tip in relation to the tube. This universal movement enables the instrument to adapt to the relative deflection of the vaginal and cervical canals in those cases where the cervix is anteriorly or posteriorly flexed, or retroverted in relation to the vagina.

These features will be better understood by reference to the accompanying drawing wherein I have illustrated one of the preferred embodiments.

BRIEF DESCRIPTION OF THE DRAWING

In the drawing:

FIG. 1 is a perspective view of the embodiment with the sampling tip being seen at the left-hand or closer end of the view;

FIG. 2 is an operative view of the embodiment after the tip has been applied to the cervix, which in this case is aligned with the vaginal canal;

FIG. 3 is another operational view of the embodiment, but in this case showing the tip only and with the cervix anteriorly flexed to illustrate the ability of the instrument to adapt to the relative deflection of the vaginal and cervical canals; and FIG. 4 is a part perspective view of the embodiment and particularly the tip as it is applied to the surface of a smear plate for purposes of transferring the scrapings thereto.

DESCRIPTION OF THE PREFERRED EMBODIMENT

Referring firstly to FIG. 1 it will be seen that the illustrated embodiment comprises an aspirator tube 2 which has a plunger 4 therein to enable a suction head to be generated at the left-hand or distal end 6 of the tube. The tube is preferably molded from a plastic resin, and in the molding process an annular flange 8 is formed on the right-hand or proximal end 10 of the tube to provide an enlarged surface 12 which can be easily gripped for rotation of the tube. Knurling or serrations on the peripheral surface 12 of the flange aid in gripping it for this purpose. The plunger 4 is essentially a small rubber piston 14 which is slidably received in the bore 16 of the tube to be advanced and retracted at the instance of a fluted plastic rod 18 extending rearwardly from the piston through the bore to a point thereoutside at which it is capped by a flanged cylinder 20. The cylinder 20 has a smaller diameter than the flange 8 of the tube, but is slightly greater in diameter than the bore 16 of the tube so as to form a limit stop for the advance of the piston 14. As seen in the figures the piston can advance only to a point short of the distal end 6 of the tube.

In molding the tube a flexible sleeve 22 is formed on the distal end thereof which is corrugated so that it can be flexed in both the transverse and axial senses with respect to the tube. However, the corrugations 24 terminate short of the sleeve's own distal end 26 so as to allow for a smooth cylindrical neck 28 thereon; and molded integrally with the neck is a spatulated sampling tip 30 having the characteristics mentioned hereinabove under the summary of the invention. The tip comprises a flat generally heart-shaped spatula 32 which has a thickness of less than the diameter of the sleeve 22, and an elongated pipette 34 passing therethrough from the neck 28 of the sleeve. The opposing heart-shaped faces 36 of the spatula are substantially parallel to the pipette, and are substantially flat across the entire profile of the spatula on each side.

The pipette 34 projects relatively forwardly from the spatula 32 and bisects the spatula into upper and lower lobes, 38 and 40 respectively, as it is seen in FIG. 1. The upper lobe 38 is somewhat larger than the lower lobe 40, and is also somewhat forwardly displaced in relation to it, as is better seen in FIGS. 2 and 3. In addition, the relatively forward edge 42 of the upper lobe has a smoothly curved indentation 44 therein which conforms to the contour of the portio vaginalis. The valley of the indentation is interconnected with the projecting portion of the pipette by a smoothly curved fillet 46 which terminates somewhat forwardly from the edge 42. The forward edge 48 of the lower lobe is also interconnected with the projecting portion of the pipette by a similar fillet 50.

During the sampling operation, a speculum is used to assist in inserting and applying the tip of the instrument. The speculum is used firstly to dilate the vaginal canal, and while it is thus employed, the physician inserts the projecting portion of the pipette 34 in the endocervical canal of the patient and abuts the valley of the indentation 44 against the surface of the portio vaginalis. Then, while gripping the flanged proximal end 8 of the aspirator tube 2 in one hand and the cylinder 20 of the plunger 4 in the other, he proceeds to collect a mucus aspirate from the internalos of the cervix, and tissue cell scrapings from the surface of the portio vaginalis. The mucus specimen is collected by retracting the plunger 4 from the tube 2; whereas the scrapings are collected by rotating the tube so as to skim the surface of the portio vaginalis with the forward edge 42 of the upper lobe 38 of the spatula. The lower lobe 40 acts as ballast to the upper lobe, and the fillets 46 and 50 serve to spread the small opening through which the pipette enters the endocervical canal. The fillet 46 of the upper lobe also collects scrapings from the mouth of the canal, and operates as a wedge to force the portio vaginalis into the valley of the indentation 44 as the instrument is rotated.

After the instrument has been withdrawn from the patient, the mucus aspirate collected in the tube 2, and the scrapings collected on the forward edge of the spatula 32 are directly applied to the surface of a smear plate or plates. In the case of the scrapings, the instrument is positioned over a narrow rectangular smear plate such as that seen at 52 in FIG. 4, and the spatula 32 is applied in short strokes over the surface of the plate until the scrapings are displaced from the edge 42 onto the plate. The sleeve 22 is sufficiently offset to the rear of the spatula and sufficiently limited in flexure that it does not interfere with the application procedure, nor the subsequent task of spreading the specimen over the surface of the plate 52 with the spatula. The mucus aspirate can be smeared over the plate with the scrapings or it can be applied to a separate plate as indicated earlier.

In those cases where the cervix is nonaligned with the vaginal canal as in FIG. 3, the limited flexure in the sleeve 22 enables the tip 30 to flex both transversely and axially in relation to the tube. Thus, the curvature and flexure in the wall of the vaginal canal do not cause discomfort to the patient, nor hamper the sampling procedure from the physician's standpoint.

The instrument is normally packaged in a sterile condition, and is mass produced for a price in the order of 10 cents per unit, so as to make it a commercially disposable item.

If desired, the pipette may be lengthened or shortened to sample the uterine cavity or the external os. In addition, many other changes and additions can be made in and to the described instrument without departing from the scope and spirit of the invention as defined in the following claims.

I claim:

1. A cervical biopsy-sampling instrument comprising an aspirator tube having a plunger therein which is equipped with means that extend from the proximal end of the tube for reciprocating the plunger within the tube, a sampling tip which is disposed at a location spaced relatively forwardly from the distal end of the aspirator tube, and which includes a pipette that is adapted to be inserted into the endocervical canal, and has a laterally projecting lobe thereon, the relatively forward edge of which lobe is adapted for scraping the portio vaginalis when the pipette is inserted into the endocervical canal, and the profile face of which on one side thereof is adapted to be used as a spatula in spreading the scrapings on a smear plate, and means interposed between the tip and the distal end of the tube which define a flexible joint whereby the tip can flex in relation to the tube, there being a passage through the joint to provide intercommunication between the pipette and the tube for withdrawing a sample of mucous from the canal into the pipette with the tube.

2. The cervical biopsy-sampling instrument according to claim 1 wherein the flexible joint includes a flexible sleeve which is interposed between the tip and the distal end of the tube.

3. The cervical biopsy-sampling instrument according to claim 2 wherein the sleeve is corrugated to allow for both limited transverse and limited axial movement of the tip in relation to the tube.

4. The cervical biopsy-sampling instrument according to claim 1 wherein the face of the lobe is substantially parallel to the pipette and substantially flat over the entire profile of the lobe on that side.

5. The cervical biopsy-sampling instrument according to claim 1 wherein the relatively forward scraping edge of the lobe has a smoothly curved indentation therein, the valley of which is interconnected with the pipette by a smoothly curved fillet which is adapted to project into the endocervical canal with the pipette.

6. The cervical biopsy-sampling instrument according to claim 1 wherein the sampling tip comprises a flat generally heart-shaped spatula which is bisected by the pipette into laterally opposing lobes having coplanar faces thereon which are substantially parallel to the pipette and substantially flat across the entire profile of the spatula on each side.

*7. A cervical biopsy-sampling instrument comprising a tube having means associated therewith whereby a suction can be generated in said tube, a sampling tip which is disposed at a location spaced relatively forwardly from the distal end of the tube, and which includes a pipette that is adapted to be inserted into the endocervical canal, and has a laterally projecting lobe thereon, the relatively forward edge of which lobe is adapted for scraping the portio vaginalis when the pipette is inserted into the endocervical canal, and the profile face of which on one side thereof is adapted to be used as a spatula in spreading the scrapings on a smear plate, and means interposed between the tip and the distal end of the tube which define a flexible joint whereby the tip can flex in relation to the tube, there being a passage through the joint to provide intercommunication between the pipette and the tube whereby a sample of mucous can be aspirated from the canal into the pipette when the suction head is applied to the tube.*

References Cited

The following references, cited by the Examiner, are of record in the patented file of this patent or the original patent.

UNITED STATES PATENTS

| | | | |
|---|---|---|---|
| 2,471,088 | 5/1949 | Ayre | 128—2 |
| 3,088,454 | 5/1963 | Shute | 128—2 |
| 3,315,661 | 4/1967 | Groat | 128—2 |
| 3,352,299 | 11/1967 | Sagiroglu | 128—2 |
| 3,438,366 | 4/1969 | Kariher et al. | 128—2 |

FOREIGN PATENTS 1,324,126 3/1963 France.

KYLE L. HOWELL, Primary Examiner

U.S. Cl. X.R.

128—278, 304